United States Patent
Meyer et al.

[11] Patent Number: 6,063,043
[45] Date of Patent: May 16, 2000

[54] ACOUSTIC VESICOURETERAL REFLUX DIAGNOSTIC SYSTEM

[75] Inventors: Martin Meyer, Raleigh, N.C.; Robert A. Mevorach, Virginia Beach, Va.

[73] Assignee: Old Dominion University Research Foundation, Norfolk, Va.

[21] Appl. No.: 09/186,596

[22] Filed: Nov. 5, 1998

[51] Int. Cl.$^7$ ........................................ A61B 5/00
[52] U.S. Cl. ................................................ 600/586
[58] Field of Search ............................ 600/595, 587, 600/593, 591, 586

[56] References Cited

U.S. PATENT DOCUMENTS

| | | | |
|---|---|---|---|
| 5,411,475 | 5/1995 | Atala et al. | 604/54 |
| 5,516,532 | 5/1996 | Atala et al. | 424/548 |
| 5,667,778 | 9/1997 | Atala | 424/93.7 |
| 5,686,425 | 11/1997 | Lee | 514/21 |
| 5,712,252 | 1/1998 | Smith | 514/21 |
| 5,958,444 | 9/1999 | Wallace et al. | 424/430 |

OTHER PUBLICATIONS

Atala et al.; Sonography With Sonicated Albumin in the Detection of Vesicoureteral Reflux, *The Journal of Urology*, 150:756–758 (1993).

Blane et al.; Renal Sonography Is Not a Reliable Screening Examination of Vesicoureteral Reflux, *The Journal of Urology*, 150:752–755 (1993).

Elder et al.; Pediatric Vesicoureteral Reflux Guidelines Panel Summary Report on the Management of Primary Vesicoureteral Reflux in Children, *The Journal of Urology*, 157:1846–1851 (1997).

*Primary Examiner*—Cary O'Connor
*Assistant Examiner*—Pamela L. Wingood
*Attorney, Agent, or Firm*—Myers Bigel Sibley & Sajovec

[57] ABSTRACT

A passive acoustic method of detecting the presence or absence of vesicoureteral reflux in a patient comprises the steps of amplifying sound from the abdomen of the patient from a time just prior to the onset of urination in the patient, and then detecting the presence or absence of an audio signal characteristic of vesicureteral reflux in the amplified sound, the presence of the signal indicating the presence of vesicoureteral reflux in the patient. Apparatus and computer program code products for carrying out the invention are also provided.

16 Claims, 7 Drawing Sheets

FIG. 10

ACOUSTIC VESICOURETERAL REFLUX DIAGNOSTIC SYSTEM

FIELD OF THE INVENTION

The present invention concerns methods, apparatus, and computer program code products useful for the noninvasive detection of vesicoureteral reflux.

BACKGROUND OF THE INVENTION

Vesicoureteral reflux is a congenital defect seen in both boys and girls that causes these children to be prone to febrile urinary tract infections. In vesicoureteral reflux, urine is propelled up the ureter toward and most times to the kidney by the increasing bladder pressure that precedes and accompanies urination. If left undiagnosed, this condition will lead to hypertension and/or kidney failure (in severe cases). Hence, it is extremely important to provide means to detect and monitor vesicoureteral reflux (VUR). The condition spontaneously resolves at a rate approaching 20% per year for lower grades of reflux, but many patients will require surgical repair or indefinite antibiotic therapy. Patients are treated with antibiotics during the condition, and the antibiotics discontinued when the condition resolves.

The most common current technique for the diagnosis and monitoring of vesicoureteral reflux is the voiding cystogram. This technique requires catheterization of the urethra, followed by filling the bladder through the catheter and fluoroscopic imaging during urination. A like procedure may be performed under a gamma camera employing a Tc99 radionuclide, which reduces radiation exposure but maintains the invasive nature of the study. There are numerous problems with such techniques: the children are required to undergo a painful and traumatic catheterization; the children are exposed to potentially harmful ionizing radiation, and the procedure is expensive to perform (being dependent on expensive imaging equipment typically housed at a hospital). Hence, patients seek to avoid this test. Risks associated with skipping tests are, however, scarring of the kidney, hypertension, renal failure, and infection (including death in serious cases). This test is so common that a small children's hospital in a mid-sized city can perform on the order of 1500 voiding cystograms each year.

Indirect cystography systems for detecting VUR utilize an injected contrast media, such as a Technetium 99 radionuclide, that fills the bladder after being processed through the kidneys. This technique eliminates the need for catheterization, but decreases the sensitivity of the test by 33% in the process. Further, the child must have an intravenous catheter inserted and is still exposed to ionizing radiation.

Ultrasound imaging systems for detecting VUR require neither catheterization nor radiation exposure, but are not reliably effective as diagnostic tools due to low sensitivity. See, e.g., C. Blane, *Renal Sonography is Not a Reliable Screening Examination for Vesicoureteral Reflux*, J. Urology 150, 752–755 (Aug. 1993). In addition, ultrasound studies are difficult and time-consuming to perform. Indeed, standard voiding cystograms are recommended for confirmation even if an ultrasound is highly suggestive of VUR.

In view of the foregoing, there is a continued need for a simple and reliable way to detect vesicoureteral reflux that does not require catheterization, exposure to ionizing radiation, or expensive imaging hardware.

SUMMARY OF THE INVENTION

A first aspect of the present invention is a method of detecting the presence or absence of vesicoureteral reflux in a patient. The method comprises the steps of amplifying sound from the abdomen of the patient from a time just prior to the onset of urination in the patient (and to a time after the onset of urination), and then detecting the presence or absence of an audio signal (i.e., an audio signal characteristic of vesicoureteral reflux, typically a low frequency audio signal) in the amplified sound, the presence of the signal indicating the presence of vesicoureteral reflux in the patient.

A second aspect of the present invention is an apparatus useful for detecting the presence or absence of vesicoureteral reflux in a patient. The apparatus comprises a sound detector configured for positioning on the abdomen of the patient; a recorder operably associated with the sound detector and configured to provide a recorded sound signal from the abdomen of the patient; and a marker operably associated with the recorder for marking the onset of urination by the patient in association with the recorded sound signal.

A third aspect of the present invention is a method of detecting the presence or absence of vesicoureteral reflux in a patient, which may be implemented as a computer-based method. The method comprises recording an amplified sound from the abdomen of a patient suspected of being afflicted with vesicoureteral reflux, from a time just prior to the onset of urination in the patient and through subsequent urination by the patient to produce an amplified sound signal. The amplified sound signal is time marked with the time of onset of urination. The amplified sound signal is filtered (before or after time marking) to produce a filtered sound signal, and the filtered sound signal is visually displayed in combination with an indication (e.g., a visual indication) of the time marking, so that the presence or absence of an audio signal characteristic of vesicoureteral reflux in the visually displayed filtered sound signal can be determined, the presence of the signal indicating the presence of vesicoureteral reflux in the patient. Computer program products for implementing such methods are a further aspect of the invention.

The foregoing and other objects and aspects of the present invention are explained in greater detail in the drawings herein and the specification set forth below.

DETAILED DESCRIPTION OF THE PREFERRED EMBODIMENTS

This invention may be embodied in many different forms and should not be construed as limited to the embodiments set forth herein. Rather, these embodiments are provided so that this disclosure will be thorough and complete, and will fully convey the scope of the invention to those skilled in the art.

It will be understood that elements of the invention can be implemented by general and/or special purpose hardware-based system that perform the specified functions or steps, or by combinations of general and/or special purpose hardware and software instructions.

Program instructions used to carry out the present invention may be provided to a processor to produce a machine, such that the instructions that execute on the processor create means for implementing the functions specified in the illustrations. The computer program instructions may be executed by a processor to cause a series of operational steps to be performed by the processor to produce a computer implemented process such that the instructions which execute on the processor provide steps for implementing the functions specified in the illustrations. Keyboards, touchscreens, mouse/screen pointer combinations and the like all provide means for accepting selection of a particular parameter by the systems described herein. Accordingly, the figures herein support combinations of means for performing the specified functions, combinations of steps for performing the specified functions and program instruction means for performing the specified functions.

The present invention is based on the discovery that vesicoureteral reflux may be detected from a filtered, amplified audio signal obtained from the abdomen of a patient. In brief, a detectable audio peak is found in such an audio signal, the peak typically occurring just prior to external urination. A second peak following the first peak by one to three hundred milliseconds may or may not also be present in VUR patients. Without wishing to be bound to any particular theory of the instant invention, it is believed that this sound corresponds to a turbulent flow of urine from the bladder through the ureter and towards the kidney in the afflicted patient.

The term "detecting" as used herein is intended to encompass detection of vesicoureteral reflux for any purpose, including initial diagnosis of vesicoureteral reflux in a patient not previously diagnosed with this condition, confirmation of a suspected condition, monitoring of a diagnosed condition to determine whether that condition has resolved, and post-surgical evaluation of a repaired vesicoureteral reflux to assess the success of surgical correction.

Sound detected or amplified in carrying out the present invention may be recorded just prior to the onset of external urination (e.g., 1, 2, 3 or 5 seconds or more prior to the onset of external urination) and through the initiation of urination (e.g., for 1, 2, or 5 seconds or more after the onset of external urination). It is not critical to exclude extra time recording.

The term "vesicoureteral reflux" (or "VUR") as used herein is intended to encompass both unilateral (involving a single urinary collecting system) or bilateral (involving both urinary collecting systems) vesicoureteral reflux.

Patients or subjects to be treated by the present invention include both male and female patients. Patients may be of any age, but are typically children, or pre-adolescent, patients. The patients are typically human patients, but may be other mammalian animals with the invention being carried out for veterinary medical purposes.

In overview, apparatus for carrying out the present invention employs an electronic stethoscope in association with a personal computer equipped with the software, an appropriate data acquisition board, and a display. The software incorporates an adjustable filtering routine for filtering the recorded audio signal from a patient in different ways. The signal is displayed after filtering, typically after being filtered in a variety of ways, for diagnosis by the user. While it is possible to envision a variety of different ways in which the detection of the signal might be indicated, it is currently believed that the visual display of amplified signals will be most clinically useful, and most clinically acceptable. To avoid the need to visually inspect a large amount of data, a marking signal for the time of onset of urination is provided by a button input, by a marker triggered by micturition (the initiation of external urine elimination), or the like, and the visual display of the audio signal is marked by a time indication.

An audio signal characterisitic of vesicoureteral reflux typically comprises VUR peaks. VUR peaks are characterized by their discrete nature. The VUR peaks typically appear in pairs separated by a finite time interval in the range of about 10, 20, or 50 to 200, 300 or 500 milliseconds (typically about 100 milliseconds), though they can also appear as singlets, triplets, etc. The frequency range of the VUR peaks is typically a low frequency of about 50 or 100 to 400 or 800 Hertz. However, the basic nature of the reflux event will differ in rate, volume of flow, diameter of the collecting structures of the urinary system, and the pressure of voiding, all of which will result in a range of auditory VUR signatures that will be unique to each patient tested.

Figure 1:
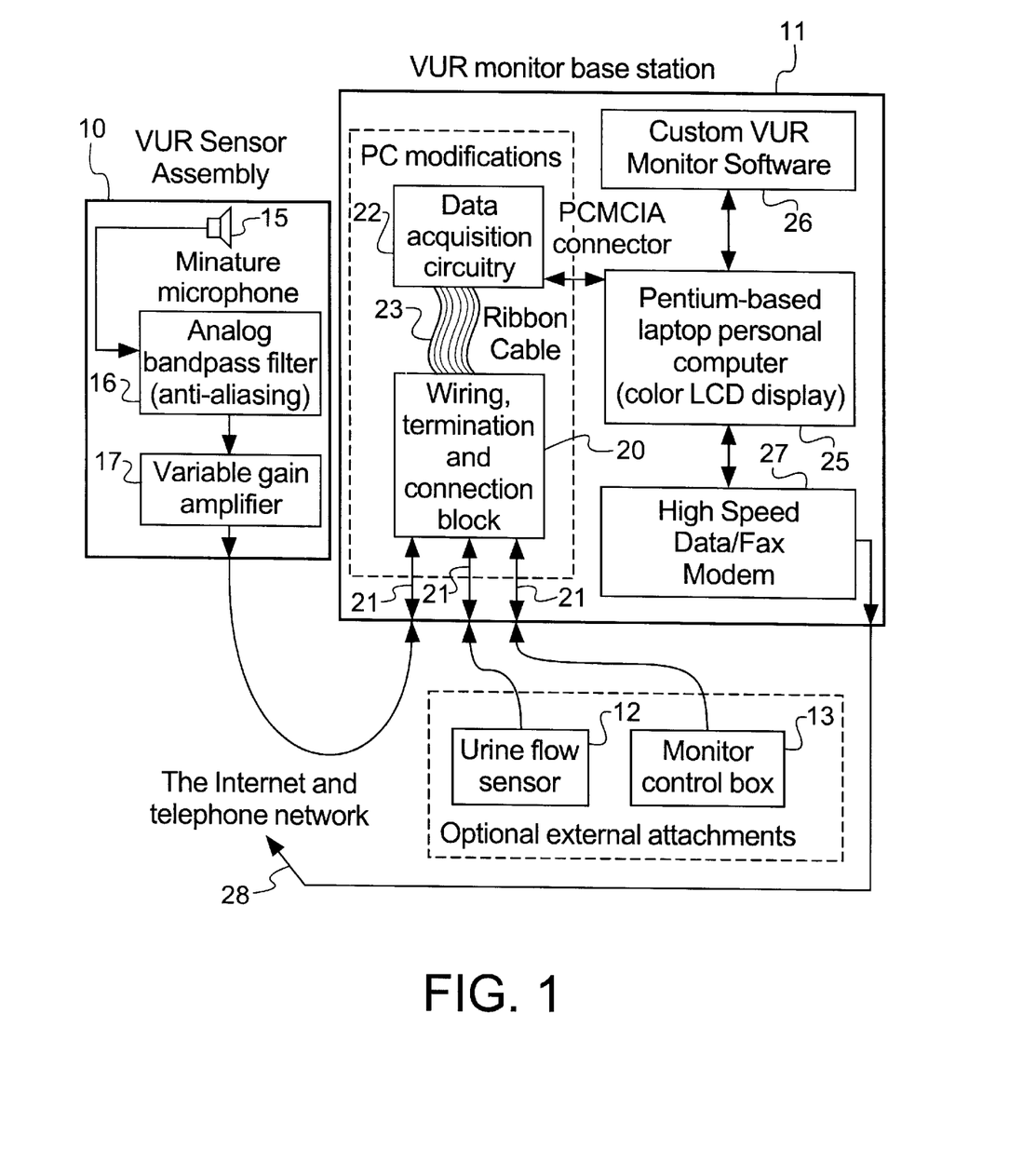
FIG. 1 schematically illustrates a first embodiment of the present invention, incorporating a VUR monitor base station.

FIG. 1 shows a system block diagram of an apparatus useful for carrying out the present invention. In general, the apparatus comprises a VUR sensor assembly 10, a VUR monitor base station 11, and optional external attachments (urine flow sensor 12 and monitor control box 13).

The VUR sensor assembly gathers pressure waves from the surface of the patient's body and converts this acoustic signal into an electrical signal with sufficient amplitude and desirable frequency characteristics. The sensor assembly comprises a miniature microphone 15 that transduces sound/pressure waves into a voltage waveform. The microphone is enclosed in a conical shaped bell to focus the sound waves, as in a conventional electronic stethoscope. An analog bandpass filter 16 is connected to the microphone, the bandpass filter removing excess background noise and preventing aliasing by bandlimiting the signal for effective sampling and digitization. Two selectable bandpass filters are used: (i) filter range 1: 100 Hz–240 Hz (−3 dB) and 45 Hz –900 Hz (−20 dB); (ii) filter range 2: 125–350 Hz (−3 dB) and 50 Hz–2000 Hz (−20 dB). The analog bandpass filter is connected to a variable gain amplifier 17, which in the preferred embodiment comprises a manually adjustable amplifier with peak output of 27 dB at 200 Hz. These components are all provided as part of a commercially available electronic available from Cardionics, inc. The conical bell housing may be formed by molding silicone caulk around the stethescope in a disposable drinking cup or the like; any baffle, cover, or other means for deadening extraneous noise may be employed in connection with and association with the microphone, if so desired.

While a single VUR sensor assembly is shown, the present invention could also be implemented with a pair of sensor assemblies, each having a separate data recording channel, so that VUR to both kidneys may be separately detected.

The VUR monitor base station (11) collects, processes, displays and stores the electrical VUR test signal received from the VUR sensor assembly. The base station includes wiring, termination, and connection block 20 which provides electrical connection and termination for cables 21 bringing data from external monitor sensors, including the VUR sensor assembly. The data acquisition circuitry 22 is connected to the connection block by ribbon cable 23 and is a multi-channel analog to digital converter which samples, digitizes and buffers up to 8 external sensors at up to 100 kHz with 12-bit resolution (a PCMCIA plugin for the laptop PC which is manufactured and sold by National Semiconductor along with the termination block and ribbon cable). The current preferred sampling rate is 5 KHz. A standard PCMCIA connector 24 connects the data acquisition circuitry to a PENTIUM™ chip-based laptop computer 25 (e.g., an IBM THINKPAD™ computer) which hosts the VUR monitor software 26 described in detail below, controls the data acquisition circuitry and stores patient data files. While the laptop computer itself provides a patient database means in the form of recorded data files for both different patients and the same patient for different sessions, a data/fax modem 27 also provides the capability to upload/download patient files to and from remote locations via means such as the internet and telephone networks 28. This is useful in situations where test data is gathered in one location and analyzed at another location. The model also allows software revisions to incorporate telemedicine functionality, for example by providing access to an external database, or by providing a means to forward information to a remote physician. The VUR monitor software (discussed below) provides a graphical user interface and an environment for configuring test parameters, naming patient data files, displaying test results, inserting event markers, and analyzing test results. Also, the software integrates inputs from optional external attachments and provides the capability to perform digital filtering and automated signal enhancement to aid in the offline diagnosis of VUR.

Figure 2:
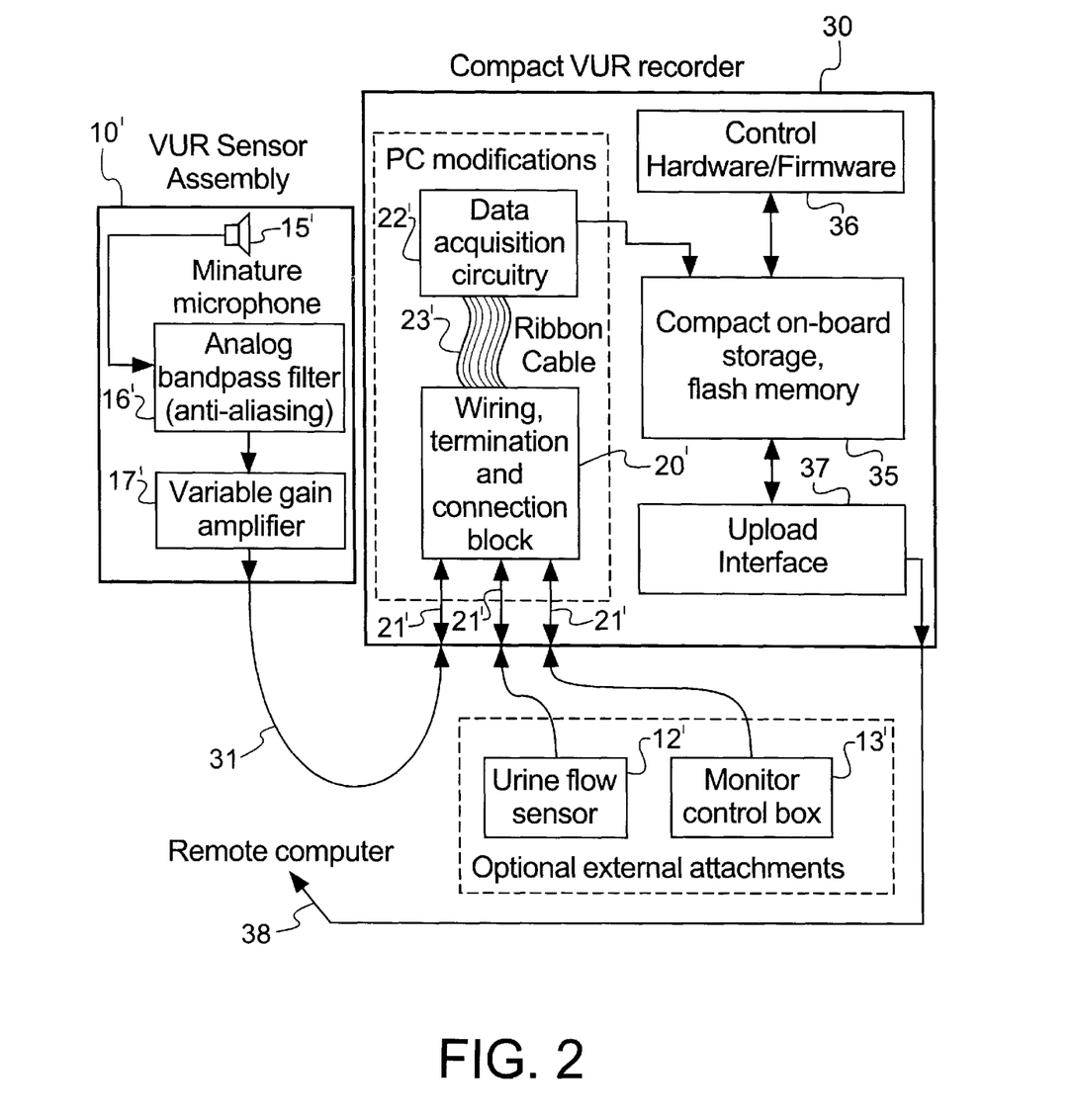
FIG. 2 schematically illustrates a second embodiment of the present invention, configured to provide access to a remote base station or computer so that the embodiment is portable.

An alternate embodiment of the invention is illustrated in FIG. 2. The VUR sensor assembly and the optional external attachments are essentially the same as illustrated in connection with FIG. 1 above, and like components are assigned like numbers in FIGS. 1 and 2 with the FIG. 2 numbers simply including a prime (') designation. The VUR monitor base station is, however, replaced with a compact VUR recorder 30. A wiring, termination and connection block 20' is provided as in FIG. 1, along with data acquisition circuitry 22'. A compact on-board storage with flash memory 35 is provided, along with an upload interface 37 and control hardware/firmware 36. The circuitry designated within the compact VUR record 30 can be provided in a compact housing with the VUR sensor assembly 10 connected thereto by cable 31, and the unit so formed attached to a halter like a cardiac halter monitor to provide a wearable carrying means (of course any system of straps, belt loops, garment, or the like to which the housing containing the compact VUR record 30 is attached can serve as the wearable carrying means). Dual VUR sensor assemblies can be included if desired as described above. This unit provides a low cost alternative for conducting a test in a medical center, with the subsequent offline analysis and diagnosis being performed elsewhere by a remote computer 38.

Figure 4:
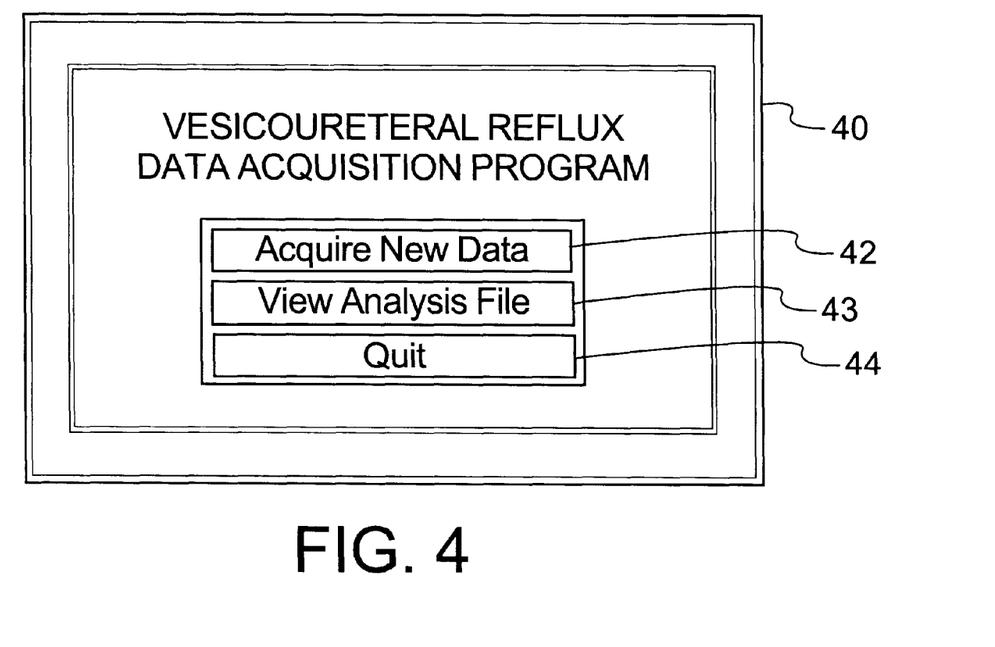
FIG. 4 illustrates the main screen of software of FIG. 3.
Figure 5:
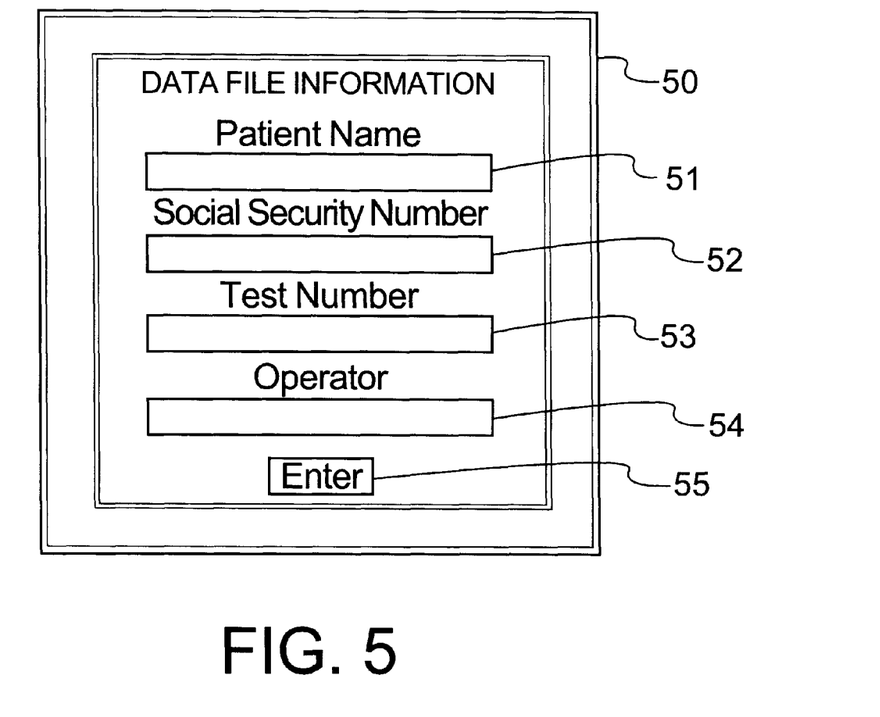
FIG. 5 illustrates the data information screen of software of FIG. 3.
Figure 6:
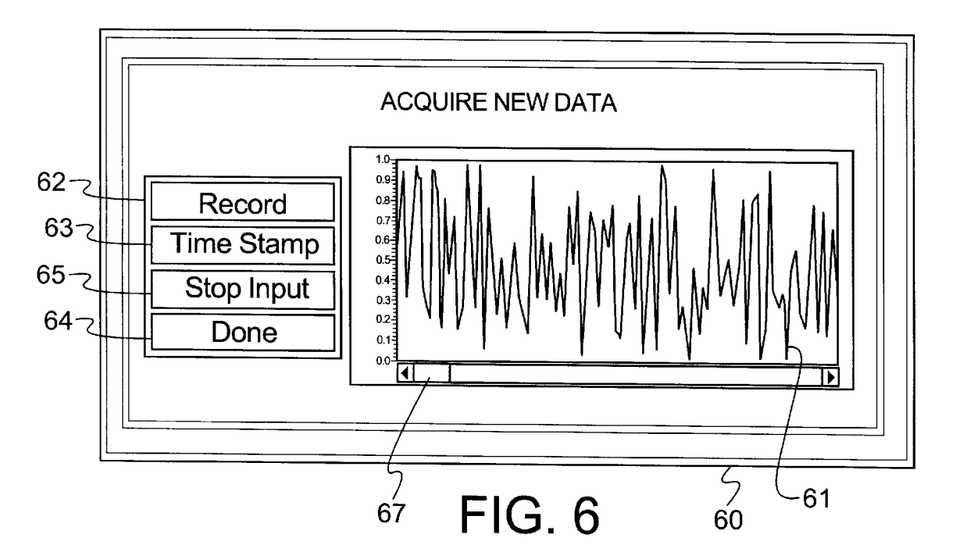
FIG. 6 illustrates the acquire new data screen of software of FIG. 3.
Figure 7:
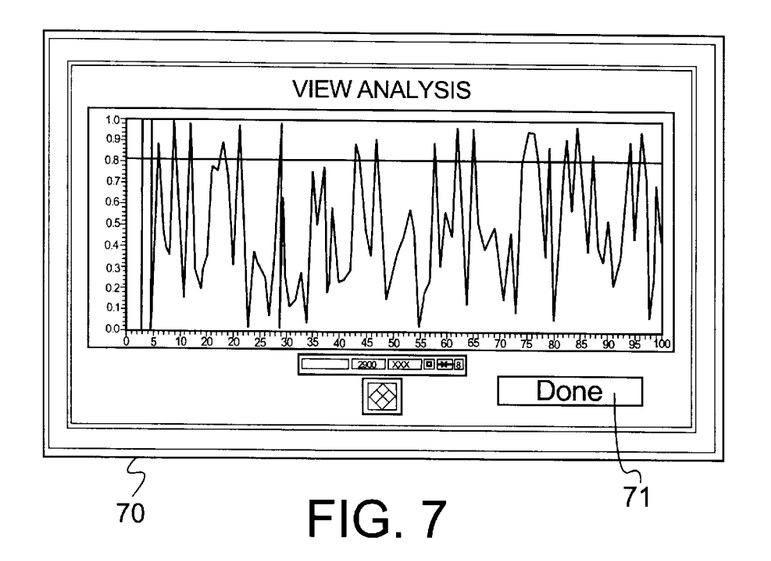
FIG. 7 illustrates the view analysis file screen of software of FIG. 3.

The monitor software (schematically illustrated in FIG. 3) provides an interface between the monitor hardware and the clinical personnel performing tests of the invention. The software is preferably compatible with the Windows 95 and Windows NT operating systems. In a preferred embodiment, the LabVIEW language (available from National Semiconductor) is used to create the custom monitor software. As illustrated herein, the user interacts with the program through a series of self-explanatory screens via the mouse and keyboard (or optional external control box). The program includes four screens: Main (FIG. 4), Acquire New Data (FIG. 5), Data File Information (FIG. 6), and View Analysis File (FIG. 7).

Figure 3:
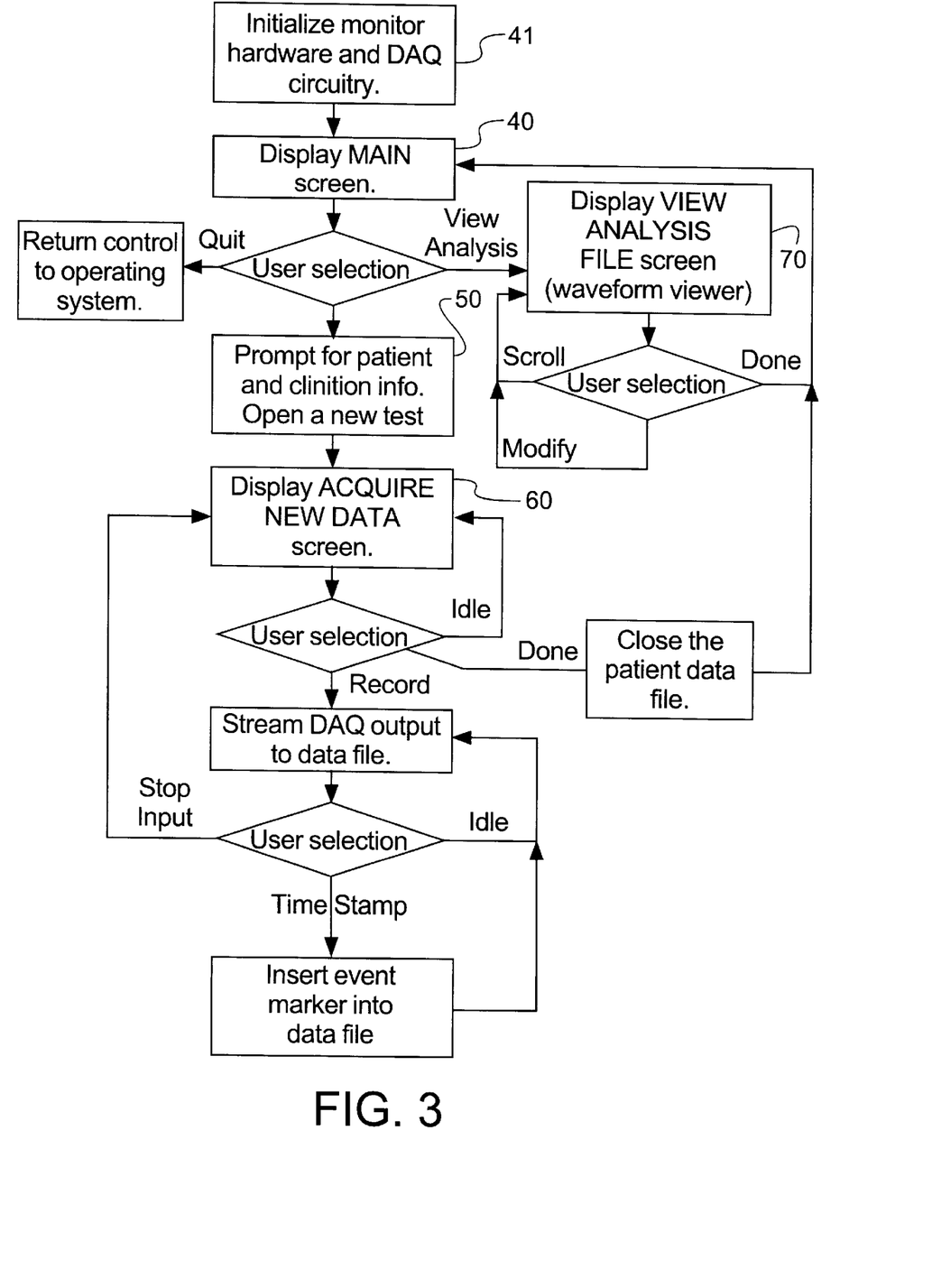
FIG. 3 schematically illustrates software useful for carrying out the present invention.

FIG. 3 shows the functional operation of the monitor software in flowchart form. The software, monitor and data acquisition (DAQ) circuitry are initialized 41 by standard techniques. Then, the Main screen 40 (FIG. 4) is accessed by double-clicking an icon on the desktop. Once the main screen program is running, the operator has three options selectable with graphical buttons: Acquire New Data 42, View Analysis File 43, or Quit 44.

The data information screen (FIG. 5) first prompts the user to select a filename for the data to be recorded. The user has the option to create a new file or replace an existing file. The menu then requests information unique to the current test including the patient's name, social security number, test number, and operator (shown by fields 51, 52, 53, 54 in FIG. 5). This information is optional and is stored in a tab-delimited spreadsheet format along with the date of the test. After the information requested is complete the user then selects the Enter button 55 to proceed to the Acquire New Data Screen 60 (FIG. 6). In this screen, the user has access to a real-time display of the input signal 61. At this time the operator can adjust the gain on the stethoscope for best results. After the initial setup is complete the user will push the record button 62 to begin storing data to disk. There is also a function that allows the operator to time stamp important events during the testing procedure by pushing time stamp button 63, such as the onset of urination (e.g., by placing a vertical line on the graphical data field shown in FIG. 5 or FIG. 7). This serves as a marking means operably associated with the recorder. Of course, numerous other marking means can also be employed: for example, if the recorder were a moving paper and pen recorder, the marking means could be a seaparate pen on the moving paper.

When the recording session is completed the stop input button 65 is pushed. At this time the operator has the option to view the recorded signal via a scrollbar 67 located at the bottom of the chart. Selecting the done button 64 returns the user to the main screen.

Selection of the view analysis file button 43 allows the user to view a previously recorded test. After pushing the View Analysis button, the user is prompted to enter the filename for the data file to be viewed. This file is then plotted on a large graph in the view analysis file screen 70 (FIG. 7). The user then has the options of changing the axis settings or tracing the plot by control button 71, or exiting back to the main menu via the done button 71. Significantly, the time stamp placed on the data file by time stamp button 63 is displayed on the data in the view analysis file screen 70, so that data collected at or about the time of urination can be detected. Where a urine flow sensor (12, 12' is employed, the file is automatically time stamped by triggering of that sensor by the urine flow).

The present invention has been illustrated by detecting the characteristic auditory signature of VUR and displaying it by visual, graphical means. This type of display is presently considered most suitable for diagnostic purposes. A convenient feature of this type of display is that a single data file can be filtered in different ways by the software, and multiple screens containing the same data, filtered or processed differently, can be simultaneously displayed in accordance with known techniques to facilitate inspection of the patient records and the detection of VUR. Nevertheless, other means of signaling the acoustic detection of VUR could be employed, such as a simple yes/no indicator such as a light, tone, or display of a text or symbol on a screen.

EXAMPLE 1

Acoustic Detection of VUR in a Known VUR Patient

Figure 8:
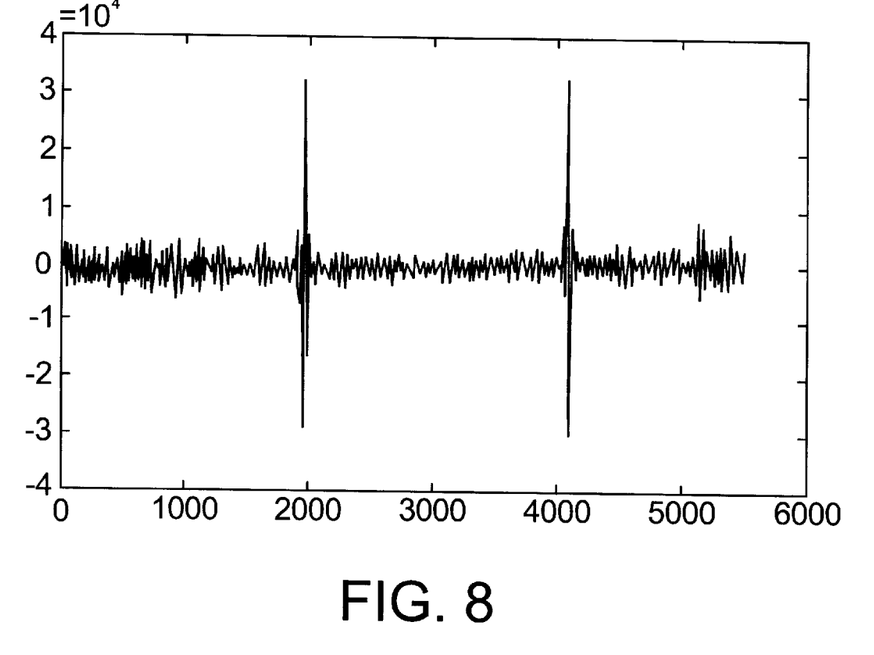
FIG. 8 illustrates data obtained from a first patient with VUR with the present invention.

A child with VUR was tested by the method of the present invention. Data collected is shown in FIG. 8. The first peak at time 2000 on the horizontal axis occured just prior to the onset of external urination.

EXAMPLE 2

Acoustic Detection of VUR in a Known VUR Patient

Figure 9:
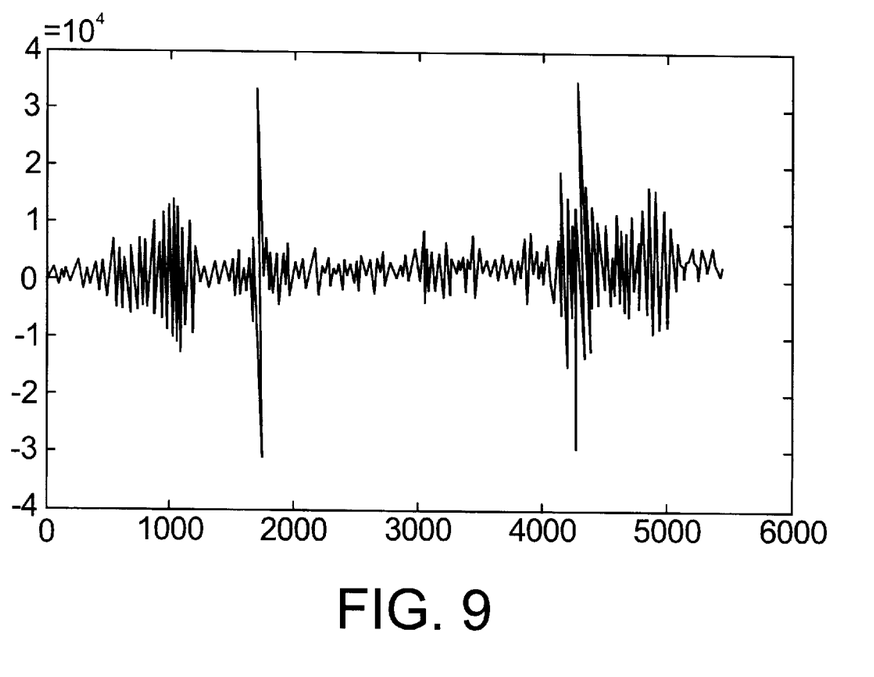
FIG. 9 illustrates data obtained from a second patient with VUR with the present invention.

A second child known to have VUR was tested by the method of the present invention. Data collected is shown in FIG. 9. As in Example 1, the first peak at time 2000 on the horizontal axis occurred just prior to the onset of external urination.

EXAMPLE 3

Acoustic Detection of VUR in a Surgically Corrected VUR Patient

Figure 10:
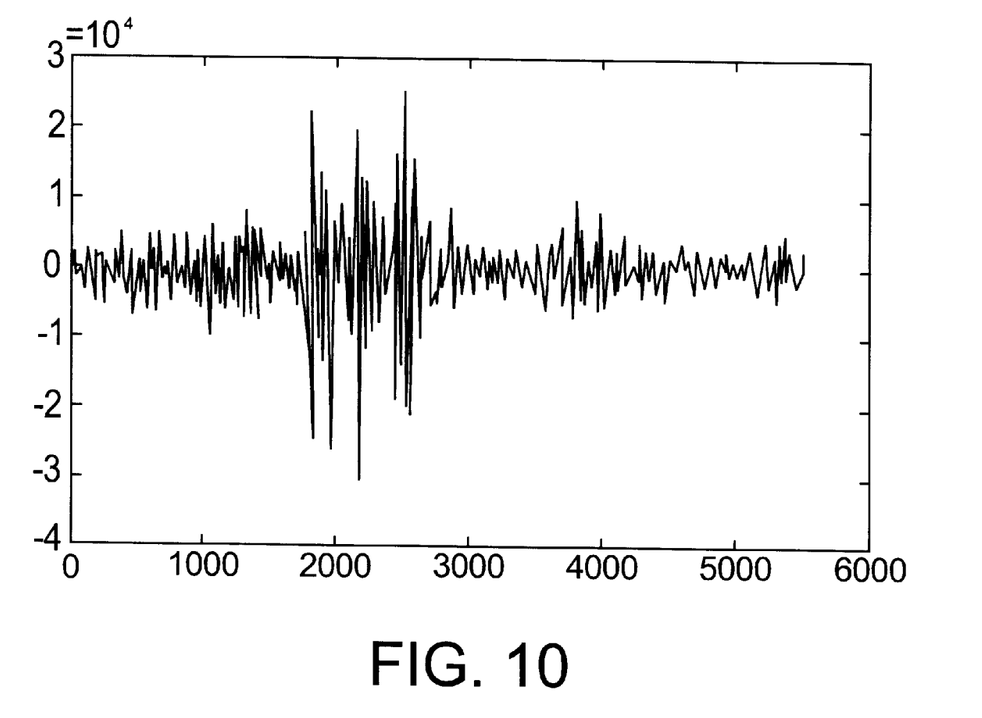
FIG. 10 illustrates data obtained from the same patient as that in FIG. 8, but after corrective surgery.

The patient of Example 1 above received corrective surgery for VUR. The surgery was confirmed to be successful. The patient was subjected to a test performed with an acoustic monitor of the present invention, and data collected is shown in FIG. 10. The peaks previously noted in Example 1 noted were found to be absent.

The foregoing is illustrative of the present invention, and is not to be construed as limiting thereof. The invention is defined by the following claims, with equivalents of the claims to be included therein.

We claim:

1. A method of detecting the presence or absence of vesicoureteral reflux in a patient, comprising:
    amplifying sound from the abdomen of said patient from a time just prior to the onset of urination in said patient; and then
    detecting the presence or absence of an audio signal characteristic of vesicoureteral reflux in said amplified sound, the presence of said signal indicating the presence of vesicoureteral reflux in said patient.

2. A method according to claim 1, wherein said amplifying step includes the step of recording said sound.

3. A method according to claim 1, wherein said detecting step is carried out by filtering said amplified sound to produce a filtered audio signal.

4. A method according to claim 3, wherein said filtering step is followed by the step of visually displaying said filtered audio signal.

5. A method according to claim 1, wherein said amplifying step is carried out through the onset of urination in said patient.

6. An apparatus useful for detecting the presence or absence of vesicoureteral reflux in a patient, comprising:
    a sound detector configured for positioning on the abdomen of said patient;
    a recorder operably associated with said sound detector and configured to provide a recorded sound signal from the abdomen of said patient; and
    marking means operably associated with said recorder for marking the onset of urination by said patient in association with said recorded sound signal.

7. An apparatus according to claim 6, wherein said sound detector comprises a pair of sound detectors, with each one of said sound detectors configured to be positioned on the abdomen of said patient adjacent each one of the kidneys of said patient.

8. An apparatus according to claim 6, further comprising:
    an adjustable band pass filter operably associated with said recorder and configured to produce a filtered audio signal.

9. An apparatus according to claim 8, further comprising display means operably associated with said filter for displaying said filtered audio signal.

10. An apparatus according to claim 9, wherein said display means is configured to simultaneously display a plurality of different filtered audio signals from the same recorded sound signal.

11. An apparatus according to claim 6, wherein said sound detector is operably associated with a band pass filter, which band pass filter is operably associated with said recorder.

12. An apparatus according to claim 6, further comprising patient database means for storing a plurality of filtered audio signals collected from said patient from prior detection sessions.

13. An apparatus according to claim 6, further comprising means for storing a plurality of different filtered audio signals collected from said patient during a single detection session.

14. A method of detecting the presence or absence of vesicoureteral reflux in a patient, comprising:
    recording an amplified sound from the abdomen of a patient suspected of being afflicted with vesicoureteral reflux, from a time just prior to the onset of urination in said patient and through subsequent urination by said patient to produce an amplified sound signal;
    time marking said amplified sound signal with the time of onset of urination; and
    filtering said amplified sound signal to produce a filtered sound signal; and then
    visually displaying said filtered sound signal in combination with an indication of said time marking, so that the presence or absence of an audio signal characteristic of vesicoureteral reflux in said visually displayed filtered sound signal can be determined, the presence of said signal indicating the presence of vesicoureteral reflux in said patient.

15. A method according to claim 14, wherein said method is a computer-based method.

16. A computer program product for detecting the presence or absence of vesicoureteral reflux in a patient, said computer program product comprising a computer-readable storage medium having computer-readable program code means embodied in the medium, the computer-readable program code means comprising:
    computer-readable program code means for recording an amplified sound from the abdomen of a patient suspected of being afflicted with vesicoureteral reflux, from a time just prior to the onset of urination in said patient and through subsequent urination by said patient to produce an amplified sound signal;
    computer-readable program code means for time marking said amplified sound signal with the time of onset of urination;
    computer-readable program code means for filtering said amplified sound signal to produce a filtered sound signal; and computer-readable program code means for visually displaying said filtered sound signal in combination with an indication of said time marking, so that the presence or absence of an audio signal characteristic of vesicoureteral reflux in said visually displayed filtered sound signal amplified sound can be determined, the presence of said signal indicating the presence of vesicoureteral reflux in said patient.

* * * * *